United States Patent
Schertiger

(10) Patent No.: US 8,206,364 B2
(45) Date of Patent: Jun. 26, 2012

(54) COLLECTING BAG HAVING IMPROVED CLOSURE AND METHOD OF MANUFACTURING SUCH A COLLECTING BAG

(75) Inventor: Lars Olav Schertiger, Fredensborg (DK)

(73) Assignee: Coloplast A/S, Humlebaek (DK)

( * ) Notice: Subject to any disclaimer, the term of this patent is extended or adjusted under 35 U.S.C. 154(b) by 794 days.

(21) Appl. No.: 12/226,136

(22) PCT Filed: Apr. 4, 2007

(86) PCT No.: PCT/DK2007/050041
§ 371 (c)(1),
(2), (4) Date: Oct. 9, 2008

(87) PCT Pub. No.: WO2007/115575
PCT Pub. Date: Oct. 18, 2007

(65) Prior Publication Data
US 2009/0143755 A1    Jun. 4, 2009

(30) Foreign Application Priority Data

Apr. 11, 2006    (DK) .................. 2006 00523

(51) Int. Cl.
*A61M 1/00*    (2006.01)
*A61F 5/44*    (2006.01)
*B65D 33/06*    (2006.01)
*B65D 33/16*    (2006.01)
(52) U.S. Cl. .......... 604/332; 604/317; 604/327; 383/27; 383/42

(58) Field of Classification Search .................. 604/327, 604/332, 345, 403, 317, 349; 383/33, 34, 383/36, 43, 46–48, 49, 50, 51, 59, 89, 91, 383/93, 94
See application file for complete search history.

(56) References Cited

U.S. PATENT DOCUMENTS 3,268,106 A    8/1966   Satz
5,968,024 A  * 10/1999   Freeman ...................... 604/334
(Continued)

FOREIGN PATENT DOCUMENTS

CN    1306408    12/1999
(Continued)

OTHER PUBLICATIONS

Office action in corresponding CN application No. 200780021745.4, Apr. 14, 2010.
(Continued)

*Primary Examiner* — Leslie Deak
*Assistant Examiner* — Xin Xie
(74) *Attorney, Agent, or Firm* — Coloplast Corp., Coloplast A/S; Daniel G. Chapik; Nicholas R. Baumann

(57) ABSTRACT

The collecting bag is intended for human body wastes and has a bag member (1) and a discharge portion (8) including a discharge opening (9). The bag member (1) and the discharge portion (8) are formed by a first and a second film blank (2, 3). A first plate member (21) is positioned on the first film blank (2) and a second plate member (22) is positioned on an extension (3e) of the second film blank (3) such that the plate members have a distance (d) between them. Two strap members (23, 24) are positioned between the first and the second plate member (21, 22).

16 Claims, 2 Drawing Sheets

U.S. PATENT DOCUMENTS

| | | | |
|---|---|---|---|
| 6,045,542 A * | 4/2000 | Cawood | 604/327 |
| 6,780,172 B2 * | 8/2004 | Olsen et al. | 604/332 |
| 6,887,222 B2 * | 5/2005 | Mandzij et al. | 604/332 |
| 7,223,260 B2 * | 5/2007 | Hansen et al. | 604/327 |
| 2003/0073962 A1 | 4/2003 | Olsen et al. | |
| 2003/0167042 A1 * | 9/2003 | Poulsen | 604/327 |
| 2004/0068243 A1 | 4/2004 | Hansen et al. | |
| 2004/0129589 A1 * | 7/2004 | Tucker et al. | 206/335 |

FOREIGN PATENT DOCUMENTS

| | | |
|---|---|---|
| WO | 99/25278 | 5/1999 |
| WO | WO 99/25278 | 5/1999 |
| WO | 99/66859 | 12/1999 |
| WO | WO 99/66859 | 12/1999 |
| WO | WO 01/28470 A1 | 4/2001 |
| WO | 03/096941 | 11/2003 |
| WO | WO 03/009641 A1 | 11/2003 |
| WO | 2004/030584 | 4/2004 |
| WO | WO 2004/030584 A1 | 4/2004 |

OTHER PUBLICATIONS

International-type Search Report in corresponding DK application No. PA 2006 00523, dated Feb. 8, 2007.

International Search Report in corresponding WO application No. PCT/DK2007/050041, dated Jul. 2, 2007.

* cited by examiner

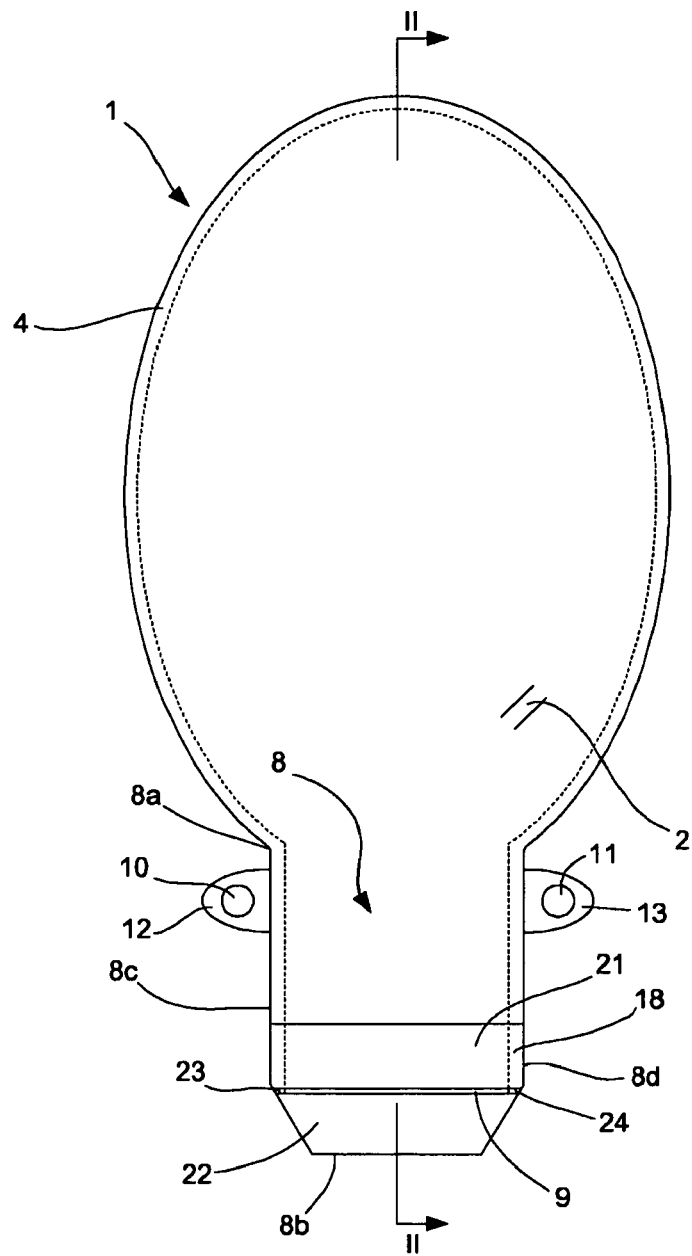
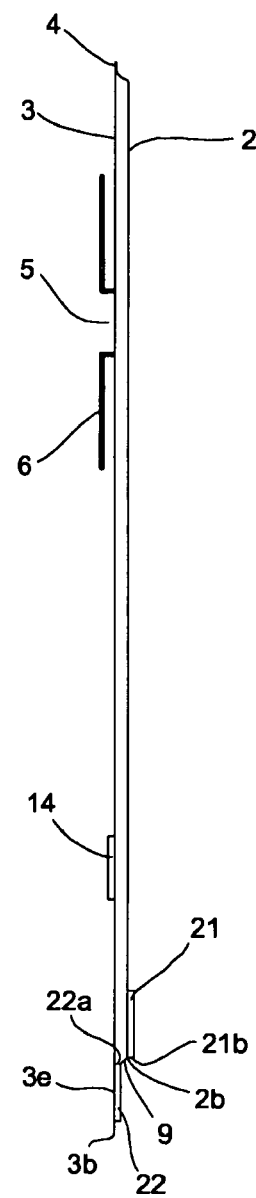
Fig. 1
Fig. 2

COLLECTING BAG HAVING IMPROVED CLOSURE AND METHOD OF MANUFACTURING SUCH A COLLECTING BAG

This is a national stage of PCT/DK07/050041 filed Apr. 4, 2007 and published in English.

FIELD OF THE INVENTION

The invention relates to a collecting bag for human body wastes, comprising a bag member, and a discharge portion including a discharge opening and having a longitudinal direction, said bag member and said discharge portion being formed by a first and a second film blank, the second of said film blanks being provided with an extension in said discharge portion, said collecting bag furthermore including a first plate member having a distal edge and a second plate member having a proximal edge, said first plate member being positioned on the first film blank and said second plate member being positioned on the extension of the second film blank, said discharge opening extending between said facing edges, said collecting bag having a position, in which said first and second plate members are situated one after the other in the longitudinal direction of said discharge portion and substantially in parallel with each other, wherein, in said position, said distal edge faces said proximal edge and said first and second plate members have a predetermined distance between the facing edges.

BACKGROUND OF THE INVENTION

This type of drainable collecting bags is often used as ostomy bags. In the case of ileostomy patients and colostomy patients with uncontrolled release of faeces of a more or less fluid consistence, the collecting bag has to be emptied rather frequently, and the closure device thus has to be easy to open and re-close after emptying and at the same time provide a reliable and tight seal in operation, i.e. between emptyings.

Several different designs of closure devices have been developed and are generally known.

Published international application No. WO 99/66859 discloses a collecting bag having one or more resilient seal members positioned at or near the discharge opening. The resilience of the member or members provides an efficient sealing effect at the beginning and the end, respectively, of the folding operation.

In a further development of this collecting bag usable in a wider range of applications, published international application No. WO 2004/030584 discloses a collecting bag of the kind mentioned in the introduction. The collecting bag disclosed in this document provides for a combination of forming the plate members from a relatively stiff material and particular positions of the plate members with respect to each other, by which the effect is obtained that the folding operation is facilitated even in case of wide discharge portions. Surprisingly, it turns out that sufficient tightness is achieved, even though virtually no deformation of the plate members in the thickness direction takes place. During the folding of the discharge portion the distal edge of the first plate member provides a pivot which, due to the thickness of the first plate member in combination with the small distance between this distal edge and the proximal edge of the second plate member, gives rise to a tensional force in the longitudinal direction of at least the second film blank and consequently, the elasticity of the film blanks provides a sealing force.

This collecting bag has proven to function well. However, as the plate members are traditionally attached to the respective film blank by means of an adhesive, the manufacture is rendered relatively cumbersome and expensive. This is underlined by the fact that the position of the plate members is relatively important in order to ensure proper function of the collecting bag and consequently, particular measures have to be taken during manufacture to secure that the plate members are positioned correctly.

SUMMARY OF THE INVENTION

With this background it is an object of the present invention to improve a collecting bag of the kind mentioned in the introduction with respect to reliability of the collecting bag during use.

It is a further object to improve the manufacturing conditions.

In a first aspect of the present invention, these and further objects are met by the provision of a collecting bag as stated in the introduction, which is furthermore characterized in that, in said position, said distance is smaller than the total thickness of the first plate member and the second plate member, and at least two strap members are provided between the facing edges and extending throughout said distance, and that the first and the second plate member are connected with each other by said at least two strap members.

The provision of the strap members has a double function of securing a proper functioning of the collecting bag during its entire period of use, and of facilitating the manufacture of the collecting bag. When manufacturing the collecting bag, the strap members provide a protection of the film blank or film blanks in the area between the facing edges of the plate members. This provides for an increased degree of freedom with respect to the choice of joining techniques. For instance, it has been made possible to utilize welding also for attaching the plate members to the respective film blank, and not only for joining the film blanks to each other. In this case the strap members absorb some of the heat necessarily involved in the welding process. In the absence of strap members this heat would deteriorate the film blank or film blanks, possibly to such an extent that the closure of the discharge portion may not be carried properly, or even that leakage occurs. Consequently, a substantial rationalization of the manufacturing process is obtained. During use of the collecting bag the strap members act as reinforcement. This entails, i.a., that the distance between the facing edges of the plate members remains substantially constant, thereby securing a reliable functioning of the collecting bag during its entire lifetime. The presence of a predetermined distance between the distal edge and the proximal edge of the first and second plate members, respectively, entails that it is possible to control the closure of the discharge portion without having to take particular precautions, as the distance may be chosen according to the materials and dimensions chosen for the film blanks, the plate members, and the strap members. The provision of a distance smaller than the total thickness of the first plate member and the second plate member ensures that there will be a tensional force acting on the second film blank when the discharge portion is folded to attain the closed folded condition. In turn, this tensional force provides a sealing force acting to press the plate members towards each other in the area of the discharge opening.

The strap members may in principle have any suitable dimensions in the height and width directions of the discharge portion as long as they fulfill the requirements of acting as a bridge between the plate members, both during manufacture to protect the film blanks and during use. In an advantageous development of this embodiment, each strap member has a height in the longitudinal direction of the discharge portion corresponding to the distance between the facing edges.

The most suitable distance between the facing edges depends of the stiffness of the plate members and of the resilience of the film blank. In general, stiffer plate members require a more resilient film blank and a larger distance. The distance may lie in the range from 25-90%, preferably 28-70%, and most preferably 30-45%, of the total thickness of the first plate member and the second plate member.

Also in the thickness direction, the strap members may have any suitable dimension, as long as the requirements mentioned in the above are fulfilled, i.e. to obtain a balance between the need for protection during manufacture and the requirements in the folding operation when the collecting bag is in use. The thickness of each strap member preferably lies in the range 50-100%, preferably 75-85%, of the distance between the distal edge of the first plate member and the proximal edge of the second plate member.

In principle, the strap members may be formed as extended, possibly reinforced, portions of one or both of the film blanks, as long as they are positioned to act as a bridge between the plate members. However, it is preferred that the thickness of each strap member be substantially larger than the thickness of each film blank, preferably in the range 0.15-1 mm.

Although the strap members may be formed as separate members, for instance as extended portions of the film blanks, it is preferred that said strap members are formed integrally with the plate members, said strap members and plate members forming a unit. Such a unit is particularly easy to handle during manufacture of the collecting bag. Furthermore, as the connection with the plate members is in this case made integral, a reliable reinforcement of the discharge portion in the particular area surrounding the facing edges of the plate members is provided. For instance, said integrated strap members and plate members may be provided as a moulded unit.

Suitable materials for use in such a unit are for instance polyethylene (PE), polypropylene (PP), a copolymer of PE and ethylene vinyl acetate (EVA), nylon or any other suitable material, or a combination of any such materials. It goes without saying that these materials may be utilized also in the case where the plate members and strap members are not provided in one unit.

In an advantageous embodiment, at least one of the facing edges of the plate members is provided with a fillet or chamfer. This provides for a springing effect when the discharge portion is folded to attain the closed folded condition. In this manner slight deviations in the positions and/or thickness of the plate members may be compensated for. Such deviations are most often due to manufacturing conditions, and may, if not compensated for, entail uneven or skew load of the film blanks, which in worst case may lead to deterioration of the film blank, possibly to such an extent that local rupture of the film blank occurs, and/or lack of tightness of the discharge portion.

Preferably, each chamfer extends in the entire width of the first and/or second plate member.

It is preferred that each chamfer extends in a part of the thickness direction of the first and/or second plate member, preferably such that the chamfer extends in a part of the facing edges in the range 30 to 70% of the thickness of the respective plate member in the area adjacent the discharge opening.

In an advantageous embodiment, the distal edge of the first plate member and the proximal edge of the second plate member are each provided with a chamfer of approximately 45 degrees extending in the entire width of the respective plate member and over approximately 50% of the thickness of each plate member.

In a second aspect a method of manufacturing a collecting bag including a bag member and a discharge portion is provided. The method comprises the steps of providing a first film blank, providing a second film blank with an extension, joining the first and second film blanks in a first continuous seam to provide the bag member, attaching a first plate member on the first film blank, attaching a second plate member on the extension of the second film blank, and is characterized in the steps of providing at least two strap members having at least the same thickness as each film blank between the plate members, and joining the first and second film blanks in a second continuous seam for providing said discharge portion having a discharge opening, said seam extending at least along side edges of the first and second plate members and along said strap members.

As the strap members provide a protection of the film blanks, it is possible to obtain a wider variety of joining techniques than would have been possible otherwise.

Preferably, said joining steps are carried out by means of a welding tool.

It is furthermore preferred that said at least two strap members and two plate members are provided as a unit, which simplifies the handling of the plate members and strap members to a considerable extent.

The unit may be provided in any suitable manner, but is preferably provided by moulding.

In order to compensate for slight variations in the dimensions of the unit, which are virtually unavoidable in any manufacturing process, said unit is preferably provided with dimensions exceeding the dimensions of the discharge portion, and the method preferably further comprises the step of removing surplus material from said unit by means of cutting, punching or the like. It is noted, however, that the strap members are of course present in the finished product.

Further features and advantages may readily be appreciated from the following detailed description.

BRIEF DESCRIPTION OF THE DRAWINGS

In the following the invention will be described in further detail with reference to preferred embodiments and the several views of the schematic drawings, in which FIG. 1 shows a plane view of an embodiment of a collecting bag according to the invention, seen from the side intended to face away from the user and in a first position;

FIG. 2 shows a longitudinal section of the collecting bag along the line II-II in FIG. 1;

DETAILED DESCRIPTION OF PREFERRED EMBODIMENTS

Figure 3:
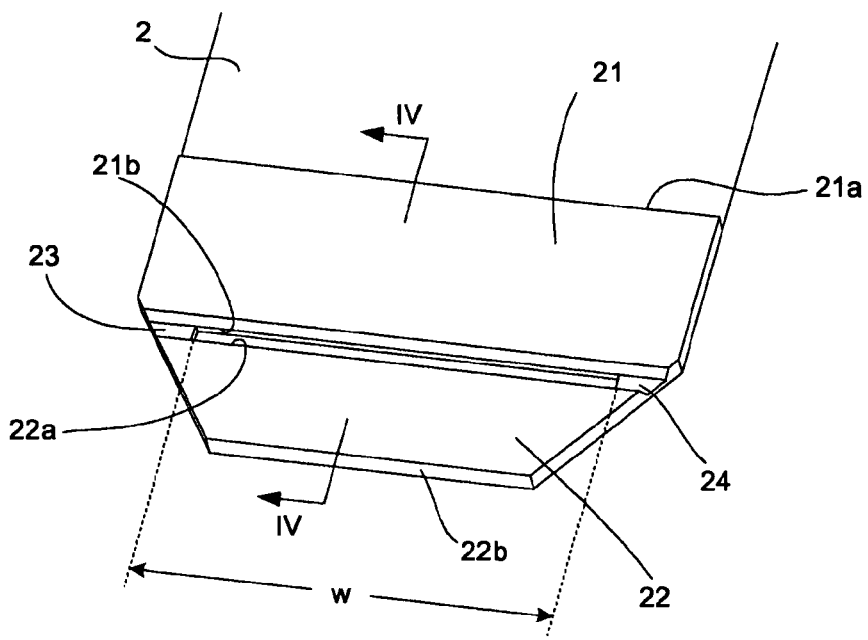
FIG. 3 shows, on a larger scale, a perspective view of a detail of the discharge portion of the collecting bag according to the invention.

In FIG. 2 some sectional areas are indicated by fully drawn lines in order not to impede the clear reading of the drawings.

The collecting bag shown in the drawings is designed as a reusable ostomy bag and comprises a bag member 1 and a discharge portion 8 having a discharge opening 9, through which the collecting bag may be emptied of its contents. The general principles relating to such an ostomy bag are well known and common. One example of an ostomy bag is, for instance, disclosed in Applicant's international published application No. WO 2004/030584.

The collecting bag may assume a number of different positions, depending on whether the bag is in its discharge position, in an intermediate position in which the bag is closed but not locked, in a position of use in which the bag is closed and locked, or in any other position. In FIGS. 1 and 2, the collecting bag assumes a position which will be referred to simply as "a first position". This first position may for instance correspond to the position the collecting bag has when it is supplied and to the position the collecting bag has just before the discharge portion 8 is opened to release the contents.

The bag member 1 and the discharge portion 8 are formed by first and second film blanks 2,3 which in a substantial part of the bag are joined along their edges in any suitable manner, preferably by means of one or more welding seams. In the embodiment shown the film blanks 2,3 in the bag member 1 are joined by one continuous seam 4, whereas the joining of the film blanks 2,3 in the discharge portion 8 is to be described further below. Preferably, and in the embodiment shown, the discharge portion 8 is formed by end sections of the film blanks of the bag member. Other solutions are possible, including those in which the film blanks of the discharge portion are made as separate film blanks joined to the film blanks of the bag member in any suitable manner.

The film blanks may be made from a suitable flexible plastic sheet or foil material. This material should to some extent be stretchable and possess at least some degree of elasticity. Each film blank 2,3 has an inner side that is intended to face the contents of the bag and an outward facing outer side. The outward facing side of the first film blank 2 is intended to face away from the user in a position of use; hence, the first film blank 2 may be said to form the front wall of the collecting bag. Correspondingly, the second film blank 3 has an outer side intended to face the user in a position of use, and thus forms the back wall of the collecting bag.

In the bag member 1, an inlet opening 5 is provided in the second film blank 3. The inlet opening 5 is, in a manner known per se, surrounded by connecting elements 6 for connection of the bag to a body orifice, i.e. in this case an intestinal orifice in the form of a so-called stoma in the user's abdominal wall.

At a distance from the inlet opening 5, the discharge portion 8 starts at a proximal or neck end 8a adjacent the bag member 1 and extends in a longitudinal direction of the discharge portion 8 to a distal or terminal end 8b. The end sections of the film blanks 2,3 are joined along opposed side edges 8c and 8d.

The second film blank 3 has dimensions corresponding to that of the entire collecting bag, i.e. including the bag member 1 as well as the discharge portion 8, and ends at a distal end edge 3b (cf. FIG. 2) coinciding with the distal end 8b of the discharge portion 8. The first film blank 2 has substantially the same dimensions in the bag member 1, but is slightly shorter than the second film blank 3 measured in the longitudinal direction of the discharge portion 8 and ends in a distal end edge 2b. As the second film blank 3 is thus relatively longer, an extension 3e of the second film blank 3 is provided.

In order to provide for sealing closure of the collecting bag, a closure device is provided in the discharge portion 8. As mentioned in the above, the fundamental principle underlying the closure mechanism in this kind of collecting bag kind is that two plate members are brought into contact with each other in an initial folding operation of the discharge portion 8 in its longitudinal direction. This will be described in further detail below.

A first plate member 21 is provided on the first film blank 2, such that a distal edge 21b of the first plate member 21 is positioned near or at the distal end edge 2b of the first film blank 2. A second plate member 22 is provided on the extension 3e of the second film blank 3 such that a proximal edge 22a is positioned opposite the distal edge 21b of the first plate member 21 such that the proximal edge 22a and the distal edge 21b face each other. In the embodiment shown, the first plate member 21 is positioned on the front side of the discharge portion 8, i.e. on the outer side of the first film blank 2, and the second plate member 22 is positioned on the front side of the discharge portion 8 as well, i.e. on the inner side of the extension 3e. Each of the first and said second plate members 21, 22 has a predetermined height in the longitudinal direction of the discharge portion between a proximal edge 21a, 22a and a distal edge 21b, 22b, respectively. The plate members 21, 22 may be connected with the respective film blank 2, 3 in any suitable manner, for instance attached to the film blanks in a welding operation as will be described in connection with the description of the manufacture of the bag. In the first position shown in FIGS. 1 and 2, the first and second plate members 21, 22 are situated one after the other in the longitudinal direction of the discharge portion 8 and substantially in parallel with each other.

The discharge opening 9, through which the bag may be emptied of its contents, is formed in the discharge portion 8. In principle, the discharge opening 9 is provided as a slit-shaped opening between the two film blanks 2,3, namely as an opening between the extension 3e of the second film blank 3 and the distal end edge 2b of film blank 2. In the embodiment shown, however, the discharge opening 9 is delimited in the longitudinal direction of the discharge portion 8 by the distal edge 21b of the first plate member 21 and thus extends between the distal edge 21b of the first plate member 21 and the proximal edge 22a of the second plate member 22, as the facing edges 21b, 22a are positioned on opposite sides of said discharge opening 9. The discharge opening 9 thus has a substantially transverse configuration relative to the longitudinal direction of the discharge portion 8 and extends from a first side to a second side. As will be described in further detail below, the discharge opening 9 is delimited in the transverse direction, substantially perpendicular to the longitudinal direction, by a strap member 23, 24 at each side of the discharge opening 9, thus making a total of two strap members. Consequently, the discharge opening 9 does not extend quite from one side edge 8c to the other side edge 8d but is separated from the side edges by the strap members.

Figure 5:
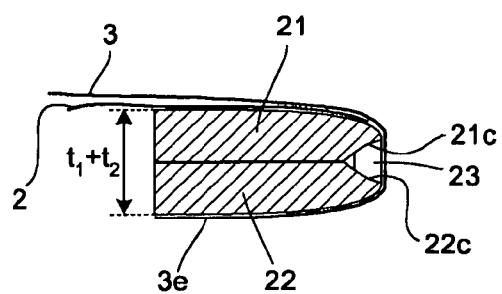
FIG. 5 shows a view corresponding to FIG. 4 of the detail of the discharge portion of the collecting bag according to the invention in a second and folded position.

In a manner known per se, the bag is brought from the open or discharge position, via the first position shown in FIGS. 1 and 2, via an intermediate closed position, a detail of the collecting bag being shown in a second and closed position in FIG. 5, to a position of use (not shown), in which the bag is closed and locked, by a number of folding operations and in a manner that will be described in further detail below.

The discharge portion 8 is foldable and unfoldable by at least one folding in its longitudinal direction between the distal and proximal ends to bring the discharge portion from an open unfolded condition to a closed folded condition and vice versa. In the first position referred to in the above, and described in connection with FIGS. 1 and 2, the collecting bag is unfolded and the plate members are situated one after the other and substantially parallel with each other. In this first position, the contents of the bag may in principle seep or flow out of the discharge opening. However, in the discharge position, in which the collecting bag is hence also in an open unfolded condition, the plate members 21, 22 may be flexed slightly by applying opposite forces to the side edges 8c, 8d of the discharge portion 8 in the area of the plate members 21, 22 such that the side edges are moved towards each other in order to enlarge the opening area. In the closed folded condition, the first and second plate members 21, 22 are in contact with each other. The term "closed" is to be interpreted as meaning sealingly closed such that virtually no material (faeces) present in the collecting bag may travel from the inside of the bag to the outside. This closed condition is attained already when the discharge portion 8 has been folded once such that the plate members have been brought into contact with each other into the above-mentioned closed folded condition. "Locked" should be interpreted to describe a condition, in which there is no need for a user to keep the discharge portion 8 in its folded position manually. Consequently, the bag will have reached its closed condition before it reaches its locked condition.

When closing the bag, the discharge portion 8 is folded starting from the distal end by initially folding the second plate member 22 against the first plate member 21, using the distal edge 21b of the first plate member 21 as a pivot. Following this initial folding, the intermediate position, which represents a closed folded condition, shown in FIG. 5 is attained. This initial folding will have a slight stretching effect on the material of the second film blank 3. During this folding, and in the intermediate position as well as in the position of use, the strap members 23, 24 connected with the film blank 3 as well as to the plate members 21, 22 act as reinforcement of the film blank 3 An effectively sealed closure of the discharge opening 9 is thus provided.

In order to keep the collecting bag in the closed and locked position, a locking device is provided, which in the embodiment shown comprises foldable locking strips 12 and 13 projecting from the side edges 8c and 8d of the discharge portion 8 at the proximal end 8a thereof. The projecting foldable locking strips 12 and 13, which may be formed integrally with one of or both the film blanks 2,3, are provided with a first set of locking means, for instance of the hook-and-loop type, which in the embodiment shown is constituted by hook elements 10,11, but which may also comprise snap fastening members, different types of adhesive members etc. and are releasably engageable with a second set of mating locking means provided on the outer side of the second film blank 3. In the embodiments shown, a plate 14 of loop elements constitutes the second set of locking means. It should be noted that the locking device may be designed in other ways, e.g. as described in applicant's International application No. WO 99/25278, or as a traditional locking clip.

Consequently, following the initial folding the discharge portion 8 is folded again, in the embodiment shown two more times, until the locking means 14 are brought into alignment with the projecting locking strips 12 and 13 which are then folded to bring the locking means 10 and 11 into engagement with locking means 14.

Figure 4:
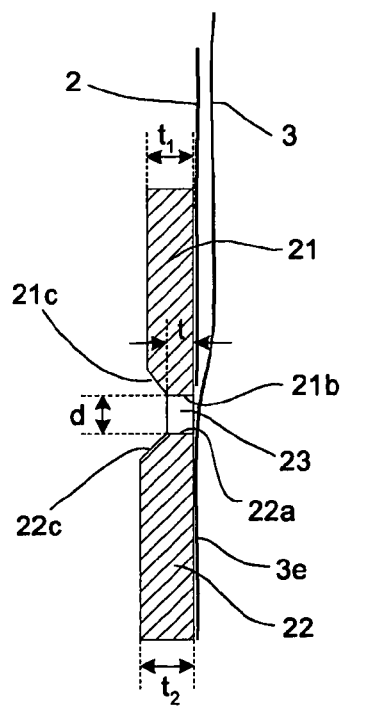
FIG. 4 shows a sectional view along the line IV-IV of the detail shown in FIG. 3.

Turning now in particular to FIGS. 3 and 4, the configuration of the plate members 21, 22 and the surrounding areas adjacent the discharge opening 9 will be described in detail.

In the position shown, the first and second plate members 21, 22 are situated in such a way on the discharge portion 8 of the collecting bag that a small clearance defining a distance d, occurs between the edges facing each other, i.e. the proximal edge 22a of the second plate member 22 and the distal edge 21b of the first plate member 21. The distance d may be predetermined according to the materials and dimensions of, i.a., the film blanks and plate members, and corresponds to the height of the strap members 23, 24 in the longitudinal direction of the discharge portion.

Generally, the predetermined distance d between the facing edges 21b, 22a should be smaller than the total sum $t_1+t_2$ of the thickness $t_1$ of the first plate member 21 and the thickness $t_2$ of the second plate member 22. Preferably, the distance d is in the range from 25-90%, preferably 28-70%, and most preferably 30-45%, of the total thickness $t_1+t_2$ of the first plate member 21 and the second plate member 22. In one example corresponding to the embodiment shown, $t_1$ is approximately 0.7 mm and $t_2$ approximately 0.9 mm in the area adjacent the discharge opening 9. As the distance d is approximately 0.5 mm, this results in a ratio of approximately 31%.

The thickness of the strap members 23, 24 is preferably chosen such that the thickness t of each strap member 23, 24 is substantially larger than the thickness of each film blank. Typical values of the thickness are 0.15-1 mm, whereas the thickness of the film blanks is approximately 75 μm (0.075 mm). As the thickness of the strap members is also related to the thickness of the plate members and to the distance d between them in order to obtain a sealing closure of the discharge portion, it is preferable to choose the thickness t in the range 50-100%, preferably 75-85%, of the distance d between the distal edge 21b of the first plate member 21 and the proximal edge 22a of the second plate member 22. In the example corresponding to the embodiment shown, the thickness t is approximately 0.40 mm, thus resulting in a ratio of approximately 80%.

In the embodiment shown the strap members 23, 24 are formed integrally with the plate members 21, 22 to form a single unit, but they may in principle be connected to the plate members 21, 22 in any suitable manner. For instance, the strap members may be formed as separate parts connected with the plate members, or as parts integral with only one of the plate members to be connected with the other plate member in any suitable manner. The strap members 23, 24 are connected with at least the second film blank 3, either in the same operation as the attachment of one or both of the plate members 21, 22 to the respective film blank, or in a separate operation. The strap members may also be made from another material than one or both of the plate members, either as co-moulded parts of another material, or as at least partly separate parts of another material, including for instance extended or folded-over portions of one or both of the film blanks of the discharge portion. It is also conceivable to form the strap members with a height, i.e. length in the longitudinal direction of the discharge portion, larger than the distance d between the facing edges to provide for an overlap of the strap members and one or both plate members. In the embodiment shown, the number of strap members is two, one at each side of the discharge opening. It is also possible to have more than one strap member in each side, e.g. two narrow strap members in a side-by-side relationship.

The strap members 23, 24 fulfill the double function of facilitating the manufacture of the collecting bag, and of securing a proper functioning of the collecting bag during its entire period of use.

As will described in further detail in connection with the below description of the method of manufacture, the strap members serve to protect the film blanks during the joining operation. The advantages obtained during manufacture are increased even further in the embodiment comprising strap members integral with the plate member; in this embodiment, the strap members keep the plate members together during handling in the manufacturing process.

When the collecting bag is in use, another advantage appears: The strap members serve to increase the strength of the hinge constituted by the film blank when folding the discharge portion. Depending on the degree of stretchability and resilience in the plane of the film blanks and other factors, such as the thickness of the respective plate members, the distance d between the facing edges has a tendency to widen during use of the collecting bag, i.e. when a number of folding and unfolding operations have been carried out. The presence of the strap members makes it possible to maintain a substantially constant distance and hence secure sealing closure of the discharge portion even after a large number of folding operations.

Further measures to manage varying positions of the plate members and control the folding operation comprise providing at least one of the facing edges 21b, 22a of the plate members 21, 22 with a fillet or chamfer 21c, 22c. In the embodiment shown, each plate member 21, 22 is provided with a chamfer 21c, 22c extending in the entire width of the respective plate member 21, 22. Each chamfer 21c, 22c extends in a part of the thickness direction of the first and second plate member 21, 22, the chamfers being situated such that the facing edges 21b, 22a are substantially perpendicular to the film blanks 2 and 3 at the connection of the plate members 21, 22 to the respective film blanks 2 and 3, whereas the outward facing edges are chamfered to form a substantially funnel-shaped cross-sectional configuration. The chamfer may extend in a part of the facing edges in the range 30 to 70% of the thickness of the respective plate member in the area adjacent the discharge opening 9, here approximately 50%. The chamfer angle may vary as well, but is conveniently about 45 degrees.

This effect may be maintained or increased even further by making at least one of the facing edges softer, e.g. by co-moulding the material of the plate members with a foam material in the area adjacent the discharge portion, in addition to making the facing edges chamfered, filleted or rounded. Furthermore, it is possible to vary the degree of resilience or elasticity of at least the second film blank, or to provide the attachment between at least the second plate member and the film blank with some elasticity. The distance between the facing edges is preferably optimised with respect to thickness and stiffness of the plate members on one hand and the elasticity, tensional strength and stretchability of the film blanks on which the plate members are arranged on the other.

It might even be possible to position the plate members in such a manner that the distance between the facing edges is substantially eliminated. In this manner welding is still possible but the advantages during use are not present.

With respect to the overall shape of the plate members, the first plate member 21 has a generally rectangular shape, whereas the second plate member 22 has a generally trapezoid shape, the second plate member 22 having at the proximal edge 22a a width w corresponding substantially to the width of the first plate member 21 at the distal edge 21b.

As mentioned in further detail in Applicant's above-mentioned international published application No. WO 2004/030584, it is possible to form the first plate member 21 with a larger height than the second plate member 22. The ratio between the heights of the first and the second plate member may e.g. lie in the interval from 1:1 to 4:1 depending on the height of the first plate member. The second plate member 22 should, however, have such a height that it has sufficient torsional strength and stability in order to allow the folding operations to be carried out properly. The width of each of the plate members 21,22 should be larger than the distance between the joints at each side edge 8c,8d and may e.g. be such that the plate members extend over the entire width of the discharge portion. The dimensions of the first plate member may vary, e.g. within an interval of the height-width ratio ranging from 1:7 to 1:2.

Furthermore, it is noted that the first plate member 21 may have a recess delimiting an area corresponding in substance to the shape of the second plate member 22. Although the thickness of the first plate member 21 is only reduced to some extent in the area adjacent the discharge opening 9, such a recess may provide for partial accommodation of the second plate member 22 when the discharge portion 8 has been folded to bring the first and second plate members 21, 22 into contact with each other.

The manufacture of the collecting bag in general and of the plate members at the discharge portion in particular will now be described in further detail.

In short, the method comprises the steps of providing a first film blank, providing a second film blank with an extension, joining the first and second film blanks in a first continuous seam to provide the bag member, attaching a first plate member on the first film blank, and attaching a second plate member on the extension of the second film blank. The steps particular to the inventive method include the steps of providing at least two strap members having at least the same thickness as each film blank between the plate members, and joining the first and second film blanks in a second continuous seam for providing said discharge portion having a discharge opening, said seam extending at least along side edges of the first and second plate members and along said strap members.

As mentioned in connection with the description of FIGS. 1 to 5, it is preferred that the strap members and plate members are provided as a unit, preferably by means of moulding. The unit is preferably provided with dimensions exceeding the dimensions of the discharge portion, further comprising the step of removing surplus material from said unit by means of cutting, punching or the like.

The plate members 21, 22 and the strap members 23, 24, whether or not they are provided as an integrated unit, may be made from a suitable material, such as polyethylene (PE), polypropylene (PP), a copolymer of PE and ethylene vinyl acetate (EVA), nylon. The plate members and the strap members may e.g. be formed from the same material as the film blanks, although in a considerably larger thickness. The plate members may be made from identical materials and have the same thickness, or possess different properties in varying areas of the plate members.

Referring to the principles set out in the above and to the embodiment shown in FIGS. 1 to 5, the collecting bag may be manufactured in the following manner:

1) The material to form the second film blank 3 is unwound from a roll.
2) An aperture is punched to form the inlet opening 5.
3) Connecting elements 6 are attached to the second film blank 3.
4) The material to form the first film blank 2 is unwound from another roll.
5) The first and second film blanks are joined to each other by means of a first welding operation to provide the seam 4 to form the bag member.
6) In the area of the discharge portion 8, the second film blank 3 is folded upwards towards the bag member 1.
7) The unit comprising the plate members 21, 22 and the strap members 23, 24 is attached to the first film blank 2 by means of a welding tool in the area of the first plate member 21.
8) Following the repositioning of the second film blank 3 to the discharge portion 8, the entire discharge portion 8 is welded by means of a welding tool to provide seam 18 in the area of the strap members 23, 24 and the second plate member 22.

9) Surplus material surrounding the contours of the finished collecting bag is removed in a punching operation.

During step 7) the second film blank 3 is not affected at all, and during step 8) the strap members 23, 24 protect the second film blank 3 by absorbing part of the heat from the welding tool.

The collecting bag may be provided with further details, such as a deodorizing filter, additional film blanks to provide a one-way valve within the bag member, comfort layers made from e.g. non-woven overlapping the outward facing sides of the film blanks, devices for retaining the folded discharge opening positioned in other places than plate 14 etc, e.g. beneath a comfort layer.

The invention should not be regarded as being limited to the embodiments described in the above but various modifications and combinations of the shown embodiments may be carried out without departing from the scope of the following claims.

For example, although the invention has been described only with reference to a collecting bag having two plate members, both of which are positioned on the outer side of the respective film blank, other configurations are conceivable as well, including those having more than two plate members and those in which it is the front film blank that is provided with an extension.

The invention claimed is:

1. A collecting bag for human body wastes, comprising:
   a bag member, and
   a discharge portion including a discharge opening and having a longitudinal direction,
   said bag member and said discharge portion being formed by a first and a second film blank, the second of said film blanks being provided with an extension in said discharge portion,
   said collecting bag furthermore including
   a first plate member having a distal edge and a second plate member having a proximal edge, said first plate member being positioned on the first film blank and said second plate member being positioned on the extension of the second film blank, said discharge opening extending between said facing distal and proximal edges,
   said collecting bag having a position, in which said first and second plate members are situated one after the other in the longitudinal direction of said discharge portion and substantially in parallel with each other,
   wherein, in said position, said distal edge faces said proximal edge and said first and second plate members have a predetermined distance between the facing distal and proximal edges,
   wherein, in said position, said distance is smaller than the total thickness of the first plate member and the second plate member, and at least two strap members are provided between the facing distal and proximal edges and extending throughout said predetermined distance, and wherein the first and the second plate member are connectable with each other by said at least two strap members such that the first plate member contacts the second plate member.

2. A collecting bag according to claim 1, wherein each strap member has a height in the longitudinal direction of the discharge portion corresponding to the distance.

3. A collecting bag according to claim 2, wherein the distance is in the range from 25-90% of the total thickness of the first plate member and the second plate member.

4. A collecting bag according to claim 3, wherein said distance is in the range from 28-70% of the total thickness of the first plate member and the second plate member.

5. A collecting bag according to claim 4, wherein said distance is in the range from 30-45% of the total thickness of the first plate member and the second plate member.

6. A collecting bag according to claim 1, wherein the thickness of each strap member is in a range of 50-100% of the distance between the distal edge of the first plate member and the proximal edge of the second plate member.

7. A collecting bag according to claim 1, wherein the thickness of each strap member is substantially larger than the thickness of each film blank.

8. A collecting bag according to claim 1, wherein the thickness of each strap member lies in the range 0.15-1 mm.

9. A collecting bag according to claim 1, wherein said strap members are formed integrally with the plate members, said strap members and plate members forming a unit.

10. A collecting bag according to claim 9, wherein said integrated strap members and plate members are provided as a moulded unit.

11. A collecting bag according to claim 9, wherein said integrated strap members and plate members are formed by a polymer selected from the group consisting of polyethylen, polypropylene, a copolymer of polyethylene and ethylene vinyl acetate, nylon, and a combination of two polymers selected from the group consisting of polyethylene, polypropylene a copolymer of polyethylene and ethylene vinyl acetate.

12. A collecting bag according to claim 1, wherein at least one of the facing edges of the plate members is provided with a fillet or chamfer.

13. A collecting bag according to claim 12, wherein each chamfer extends in the entire width of the first and/or second plate member.

14. A collecting bag according to claim 12, wherein each chamfer extends in a part of the thickness direction of the first and/or second plate member, preferably such that the chamfer extends in a part of the facing edges in the range 30 to 70% of the thickness of the respective plate member in the area adjacent the discharge opening.

15. A collecting bag according to claim 12, wherein the distal edge of the first plate member and the proximal edge of the second plate member are each provided with a chamfer of approximately 45 degrees extending in the entire width of the respective plate member and over approximately 50% of the thickness of each plate member.

16. A collecting bag according to claim 1, wherein the strap members provided a bridge between the facing distal and proximal edges of the first and second plate members, respectively.

* * * * *